(12) United States Patent
Manneck et al.

(10) Patent No.: US 10,869,816 B2
(45) Date of Patent: Dec. 22, 2020

(54) POWDER ADDITIVE TO REDUCE THE DAMAGE OF BLEACHING AND COLOURING AGENTS

(71) Applicants: Henkel IP & Holding GmbH, Duesseldorf (DE); Henkel AG & Co. KGaA, Duesseldorf (DE)

(72) Inventors: Hartmut Manneck, Barnitz (DE); Thomas Hippe, Appen (DE); Marc Stucky, Rancho Palos Verdes, CA (US); Stephanie Smith, Santa Monica, CA (US); Robert Schaeffler, Marina del Rey, CA (US)

(73) Assignees: Henkel IP & Holding GmbH; Henkel AG & Co. KGaA

( * ) Notice: Subject to any disclaimer, the term of this patent is extended or adjusted under 35 U.S.C. 154(b) by 0 days.

(21) Appl. No.: 16/397,988

(22) Filed: Apr. 29, 2019

(65) Prior Publication Data

US 2020/0337950 A1    Oct. 29, 2020

(51) Int. Cl.

| A61K 8/02 | (2006.01) |
|---|---|
| A61K 8/36 | (2006.01) |
| A61K 8/362 | (2006.01) |
| A61K 8/365 | (2006.01) |
| A61K 8/44 | (2006.01) |
| A61K 8/25 | (2006.01) |
| A61K 8/65 | (2006.01) |
| A61K 8/64 | (2006.01) |
| A61K 8/58 | (2006.01) |
| A61K 8/92 | (2006.01) |
| A61Q 5/06 | (2006.01) |
| A61Q 5/08 | (2006.01) |
| A61Q 5/10 | (2006.01) |

(52) U.S. Cl.
CPC ............ *A61K 8/022* (2013.01); *A61K 8/0225* (2013.01); *A61K 8/25* (2013.01); *A61K 8/36* (2013.01); *A61K 8/362* (2013.01); *A61K 8/365* (2013.01); *A61K 8/44* (2013.01); *A61K 8/58* (2013.01); *A61K 8/64* (2013.01); *A61K 8/65* (2013.01); *A61K 8/92* (2013.01); *A61K 8/922* (2013.01); *A61Q 5/065* (2013.01); *A61Q 5/08* (2013.01); *A61Q 5/10* (2013.01); *A61K 2800/412* (2013.01); *A61K 2800/524* (2013.01); *A61K 2800/5922* (2013.01); *A61K 2800/805* (2013.01)

(58) Field of Classification Search
None
See application file for complete search history.

(56) References Cited

U.S. PATENT DOCUMENTS

| 9,980,891 | B2 | 5/2018 | Manneck et al. | |
|---|---|---|---|---|
| 2003/0012751 | A1 | 1/2003 | Hoeffkes et al. | |
| 2004/0235700 | A1* | 11/2004 | Legrand | A61K 8/22 510/302 |
| 2017/0151142 | A1* | 6/2017 | Scheunemann | A61K 8/36 |
| 2017/0151143 | A1* | 6/2017 | Scheunemann | A61K 8/23 |
| 2017/0181946 | A1 | 6/2017 | Manneck et al. | |
| 2017/0340549 | A1* | 11/2017 | Anderheggen | A61K 8/022 |
| 2019/0070087 | A1* | 3/2019 | Cornwell | A61K 8/362 |

* cited by examiner

*Primary Examiner* — Sin J Lee
(74) *Attorney, Agent, or Firm* — P. Scott Smith

(57) ABSTRACT

A powder additive for a keratin fiber coloring or bleaching agent or developer is provided. The powder additive includes a dicarboxylic acid containing from about 2 to about 10 carbon atoms, selected from the group of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof. The powder additive also includes an amino acid or a salt of an amino acid and an alkalisilicate. The powder additive has no greater than about 10% by weight water, based on the weight of the powder additive. In addition, the powder additive includes particles and at least about 80% of the particles have an average particle size of less than 200 μm.

13 Claims, No Drawings

POWDER ADDITIVE TO REDUCE THE DAMAGE OF BLEACHING AND COLOURING AGENTS

FIELD OF THE INVENTION

The technical field relates to powder additives and methods of producing the same, and more particularly relates to powder additives for bleaching and coloring agents and methods of producing the same.

BACKGROUND OF THE INVENTION

During the coloring or bleaching of keratinous fibers, such as hair, a problem concerning damage to the keratinous fibers can occur due to the aggressive agents employed. In particular, the natural hydrophobic nature of the keratinous fiber is reduced, because the coloring or lightening agent initially has to render the fibers capable of being penetrated, so that it can take effect. With respect to hair, however, the water-repellent nature on the one hand provides the hair with a natural protection, and on the other hand is closely linked to characteristics that are desirable to the consumer, such as shine, smoothness, feel and "flow" of the hair.

To overcome the disadvantages mentioned above, what are known as pre-treatment agents are commercially available that are intended to protect the hair from the aggressive effects of coloring and bleaching. However, they frequently make the hair heavier or have a deleterious influence on the success of the subsequent lightening or coloring of the hair; in particular, the color fastness to washing could be impaired by the pre-treatment agent. In addition, many post-treatment agents are known; these are used to attempt to repair the damage to the hair caused by the coloring treatment. All these methods, however, demand a multi-step application method, namely an application of a further hair treatment agent either before or after coloring. The consumer often views this as tedious, because the coloring treatment alone is very time-consuming as it involves several operational steps and a treatment time of up to about 60 minutes.

Aqueous hair-protecting components that overcome the damaging effects of coloring or bleaching agents are known. Such components can be added directly to the coloring or bleaching agents before the agents are applied to the hair, thus avoiding an extra treatment step. However, because these additives are aqueous, they typically are formulated for a particular coloring or bleaching agent or agent product line and thus are not flexibly useful across a variety of product lines. In addition, because they are aqueous, they require the use of preservatives to maintain shelf-life.

Accordingly, it is desirable to provide a powder additive for a coloring or bleaching agent or developer to reduce damage to the hair. In addition, it is desirable to provide a method for forming a powder additive for addition to a coloring or bleaching agent or developer. Furthermore, other desirable features and characteristics will become apparent from the subsequent detailed description and the appended claims, taken in conjunction with the accompanying drawings and the foregoing technical field and background.

BRIEF SUMMARY OF THE INVENTION

In accordance with an embodiment, a powder additive for a keratin fiber coloring or bleaching agent or developer is provided. The powder additive comprises a dicarboxylic acid containing from about 2 to about 10 carbon atoms, selected from the group of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof. The powder additive also comprises an amino acid or a salt of an amino acid and an alkalisilicate. The powder additive has no greater than about 10% by weight water, based on the weight of the powder additive. In addition, the powder additive comprises particles and at least about 80% of the particles have an average particle size of less than 200 µm.

In accordance with another embodiment, a method for producing a powder additive for a keratin fiber coloring or bleaching agent or developer is provided. The method comprises combining the following ingredients and forming a mixture: a dicarboxylic acid containing from about 2 to about 10 carbon atoms, selected from the group of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof an amino acid or a salt of an amino acid; and an alkalisilicate. The method further comprises passing the mixture through a first mesh, the first mesh configured to permit particles of the mixture having an average particle size less than about 200 microns to pass therethrough. A resulting powder additive has particles of which at least 80% have an average particle size of less than 200 microns. The resulting powder additive also has no greater than about 10% by weight water, based on the weight of the resulting powder additive.

In accordance with yet another embodiment, a powder additive for a keratin fiber coloring or bleaching agent or developer is provided. The powder additive comprises a dicarboxylic acid containing from about 2 to about 10 carbon atoms, selected from the group of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof. The powder additive also comprises an amino acid or a salt of an amino acid, an alkalisilicate, a protein hydrolysate, and a polyvalent metal salt. The powder additive has no greater than about 10% by weight water, based on the weight of the powder additive. The powder additive comprises particles and at least about 80% of the particles have an average particle size of less than 200 µm.

DETAILED DESCRIPTION OF THE INVENTION

The following detailed description is merely exemplary in nature and is not intended to limit the powder additives contemplated herein, the methods for forming the powder additives or the application and uses of the powder additives. Furthermore, there is no intention to be bound by any theory presented in the preceding background or the following detailed description.

The various embodiments contemplated herein relate to powder additives, and particularly to powder additives formulated to be added to oxidative or non-oxidative coloring agents, such as direct dyes, semi-permanent dyes, or permanent dyes, bleaching agents, developers that typically include oxidizing agents, such as, for example, hydrogen peroxide, or combinations of coloring agents and developers before application to the hair. The powder additives therefore eliminate the need for a pre-treatment or post-treatment step relative to actual hair coloring or bleaching. The powder additives serve to reduce damage to the hair during coloring or bleaching without having negative influence on the resulting color. In addition, because they are an additive that reduces hair damage during coloring or bleaching, they can be presented as an additional service to the ultimate consumer, which can bring additional revenue to the hair salon or stylist.

The powder form of the additive provides particular novelty over the prior art. Because the additive is in powder form and, thus, non-aqueous, it can be used for a variety of coloring and bleaching agents and developers and across a variety of product lines. In addition, the powder additive does not require preservatives for sustainable shelf-life. Further, without the presences of water, the powder additive weighs less than an aqueous additive and, accordingly, is less costly to ship and can be stored in smaller containers. The powder additive also represents a smaller volume of material to be added to a coloring or bleaching agent or developer than an aqueous additive, thus making it easier to mix the powder additive into the coloring or bleaching agent or developer and to apply the mixture to the hair.

The powder additives as contemplated herein contain a maximum of about 10% by weight, for example, a maximum of about 6% by weight, of free water. For the purposes of the present application, "free water" is water which is not contained in the form of water of crystallization, water of hydration or similar molecularly bound water in the powder additive. The content of water of crystallization, water of hydration or similar molecularly bound water, which is contained in the components used, does not constitute free water as contemplated herein. Free water is, for example, such water which is added to the composition as contemplated herein as a solvent, as a gel activator or as a solvent component of other active ingredients.

The powder additives as contemplated herein are made up of particles of which at least about 80%, for example, at least about 90%, such as at least about 95%, for example, 100%, have an average particle size of less than 200 microns ($\mu$m), in accordance with an embodiment. It has been found that powder additives formulated as contemplated herein and made up of particles of which at least about 80% have an average particle size less than 200 $\mu$m do not result in swelling of the hair when mixed with coloring or bleaching agents and/or developers that are applied to the hair. Powder additives as formulated herein and not meeting this particle size criteria have been shown to result in swelling. "Swelling" refers to a phenomenon during which a chemical reaction of the bleaching agent with the powder additive causes aluminum foil "packages" on the hair to swell, creating an undesirable environment for the dyeing or lightening process and decreasing the effectiveness of the dyeing or lightening process. In addition, it has been found that powder additives formulated as contemplated herein and made up of particles of which at least about 80% have an average particle size less than 200 $\mu$m do not result in spotting of the hair. Powder additives as formulated herein and not meeting this particle size criteria have been shown to result in spotting. "Spotting" refers to nonuniformity of the dye deposition on the hair strands after application and development of the coloring or lightening agents and developer on the hair. In effect, "spots" appear on the hair strands from insolubility of larger particles during the development process.

In an exemplary embodiment, the powder additive comprises at least one dicarboxylic acid containing from about 2 to about 10 carbon atoms. Dicarboxylic acids suitable for use in the powder additive include those selected from malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and a mixture thereof. Preferred dicarboxylic acids include succinic acid, malic acid, and maleic acid. Succinic acid is particularly preferred. In an exemplary embodiment, the powder additive comprises the dicarboxylic acid in an amount of about 20 weight percent (wt. %) to about 80 wt. % based on the total weight of the powder additive. In another exemplary embodiment, the powder additive contains the dicarboxylic acid in an amount of about 40 wt. % to about 70 wt. % based on the total weight of the powder additive.

The powder additive also comprises at least one amino acid, according to an exemplary embodiment. The reduced damaging effect to the hair of the coloring or bleaching agents with the powder additive mixed therein is due, at least in part, to the aforementioned dicarboxylic acid(s) in cooperation with at least one amino acid. Examples of amino acids suitable for use in the powder additive contemplated herein include glycine, arginine, lysine, histidine, asparagine, glutamine, cysteine, methionine, tryptophan, serine, alanine, aspartic acid, glutamic acid, isoleucine, leucine, phenylalanine, proline, threonine, tyrosine and valine, as well as mixtures thereof. Preferred amino acids include lysine and arginine. In an embodiment, the powder additive comprises the amino acid in an amount of about 0.01 wt. % to about 10 wt. % based on the total weight of the powder additive, such as, for example, from about 0.5 wt. % to about 5 wt. % based on the total weight of the powder additive.

The powder additive contemplated herein further comprises a neutralizing agent that neutralizes the dicarboxylic acid, in accordance with an exemplary embodiment. Suitable neutralizing agents include alkalisilicates. Examples of alkalisilicates suitable for use as neutralizing agents in the powder additive contemplated herein include sodium silicate, potassium silicate, sodium metasilicate, orthosilicate, and the like and mixtures thereof. In an embodiment, the powder additive comprises one or more alkalisilicates in an amount of about 0.01 wt. % to about 60 wt. % based on the total weight of the powder additive, such as, for example, from about 15 wt. % to about 40 wt. % based on the total weight of the powder additive.

In an optional embodiment, the powder additive contemplated herein comprises silica and/or fumed silica. The silica and/or fumed silica serves to bind to any water present in the powder additive and absorbs humidity that may contaminate the powder additive. Commercial fumed silica is sold, for example, under the trade name Aerosil® available from Evonik Industries AG of Germany. In an embodiment, the powder additive comprises the silica and/or fumed silica in an amount of about 0 wt. % to about 5 wt. % based on the total weight of the powder additive, such as, for example, 0.001 wt. % to about 5 wt. %, or from about 0.05 wt. % to about 2.5 wt. %, based on the total weight of the powder additive.

In addition to absorbing water and humidity, the silica and/or fumed silica can act as a filler, making the powder additive easier to dispense and mix with the coloring or bleaching agents or developer than if the silica and/or the fumed silica were not present. Other inert organic and nonorganic fillers that do not interact with the other ingredients of the powder additives contemplated herein can also be used. Such suitable fillers include, for example, clay, lime powder, alumina, cellulose, and the like.

The powder additive further may contain a protein hydrolysate in accordance with an optional embodiment. The protein hydrolysate in cooperation with the aforementioned dicarboxylic acid and amino acid provides an additional hair damage-reducing effect. Protein hydrolysates of plant, animal and marine origin can be used. Animal protein hydrolysates are, for example, elastin, collagen, keratin, silk and milk protein hydrolysates, which can also be present in the form of salts. Protein hydrolysates of plant origin suitable for use in the powder additive include soy, almond, rise, pea, potato and wheat protein hydrolysates.

In addition, cationized protein hydrolysates can be used, wherein the basic protein hydrolysate can originate from animals, for example from collagen, milk or keratin, from plants, for example, from wheat, maize, rice, potatoes, soya or almonds, from marine life, for example, from fish collagen or algae, or from biotechnologically obtained protein hydrolysates. The protein hydrolysates forming the basis of the cationic derivatives can be obtained from the corresponding proteins by a chemical hydrolysis, particularly alkaline or acid hydrolysis, by an enzymatic hydrolysis and/or a combination of both types of hydrolysis. Moreover, cationic protein hydrolysates are understood to include quaternized amino acids and their mixtures. Quaternization of the protein hydrolysates or the amino acids is often carried out using quaternary ammonium salts such as, for example, N,N-dimethyl-N-(n-alkyl)-N-(2-hydroxy-3-chloro-n-propyl) ammonium halides. Moreover, the cationic protein hydrolysates can also be further derivatized.

The powder additive comprises the protein hydrolysate in an amount of about 0 wt. % to about 5 wt. % based on the total weight of the powder additive, according to an embodiment. In another embodiment, the powder additive contains a protein hydrolysate in an amount of about 0.2 wt. % to about 2 wt. % based on the total weight of the powder additive.

The powder additive as contemplated herein also may comprises a polyvalent metal salt of an organic acid, in accordance with an embodiment. The polyvalent metal salt provides an additional hair damage-reducing effect in combination with the dicarboxylic acid and amino acid described above. Examples of polyvalent metal salts suitable for use in the powder additive contemplated herein include polyvalent metal salts of citric acid, lactic acid, tartaric acid, and the like, such as, for example, trimagnesium citrate. In an embodiment, the powder additive comprises the polyvalent metal salt in an amount of about 0 wt. % to about 10 wt. % based on the total weight of the powder additive, such as, for example, from about 0.1 wt. % to about 5 wt. % based on the total weight of the powder additive.

Optionally, the power additive as contemplated herein may contain a saturated, non-volatile oil. These oils serve to de-dust the ingredients of the powder additives. In the case of cosmetic oils, volatile and non-volatile oils are distinguished from each other. Non-volatile oils are understood to mean those oils which have a vapor pressure of less than 2.66 Pa (0.02 mm Hg) at 20° C. and an ambient pressure of about 1013 hPa. Volatile oils are understood to mean those oils which have a vapor pressure of about 2.66 Pa to about 40000 Pa (from about 0.02 mm to about 300 mm Hg) at 20° C. and an ambient pressure of about 1013 hPa.

Oils suitable for use as contemplated herein include ester oils, such as, for example triethyl citrate. Examples of other suitable ester oils are esters of linear or branched saturated fatty alcohols having 2 to 30 carbon atoms with linear or branched saturated fatty acids having 2 to 30 carbon atoms which may be hydroxylated. Examples thereof include isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Also suitable are isopropyl isostearate, isooctylstearate, isononyl stearate, isocetyl stearate, isononyl isononanoate, isotridecyl isononanoate, cetearyl isononanoate, 2-ethylhexyllaurate, 2-ethylhexyl isostearate, 2-octyldodecyl palmitate, butyl octanoic acid, 2-butyloctanol, n-butyl stearate, n-hexyl laurate, and ethylene glycol dipalmitate.

Further suitable oils as contemplated herein are selected from the dicarboxylic acid esters of linear or branched $C_2$-$C_{10}$-alkanols. Examples include diisopropyl adipate, di-n-butyl adipate, di-(2-ethylhexyl) adipate, dioctyl adipate, diethyl/di-n-butyl/dioctyl sebacate, diisopropyl sebacate, dioctyl malate, diisooctyl succinate, di-2-ethlhexyl succinate and di-(2-hexyldecyl) succinate.

Further suitable oils contemplated herein are selected from the addition products of about 1 to about 5 propylene oxide units to monohydric or polyhydric $C_8$-C22 alkanols such as octanol, decanol, decanediol, lauryl alcohol, myristyl alcohol and stearyl alcohol. Examples include PPG-2 myristyl ether and PPG-3 myristyl ether.

Further suitable oils as contemplated herein are selected from the addition products of at least 6 ethylene oxide units and/or propylene oxide units to mono- or polyhydric $C_3$-$C_{22}$ alkanols such as glycerol, butanol, butanediol, myristyl alcohol and stearyl alcohol, which may be esterified if desired. Examples of such oils include PPG-14-butyl ether, PPG-9-butyl ether, PPG-10-butanediol, PPG-15 stearyl ether and glycereth-7 diisononanoate.

Other suitable oils as contemplated herein are selected from natural and synthetic hydrocarbons, such as mineral oils, paraffin oils, and $C_{18}$-$C_{30}$ isoparaffins. Further suitable oils include $C_8$-$C_{16}$ isoparaffins, in particular isodecane, isododecane, isotetradecane and isohexadecane, and mixtures thereof, and 1,3-di-(2-ethylhexyl) cyclohexane.

Natural oils also are suitable for use in the powder additives contemplated herein. Examples of natural oils suitable for use herein are selected from amaranth oil, apricot kernel oil, argan oil, avocado oil, babassu oil, cottonseed oil, borage seed oil, camelina oil, thistle oil, peanut oil, pomegranate kernel oil, grapefruit seed oil, hemp oil, hazelnut oil, locust seed oil, jojoba oil, linseed oil, macadamian nut oil, corn oil, almond oil, marilla oil, evening primrose oil, olive oil, palm oil, palm kernel oil, paranut oil, pecan oil, peach kernel oil, rape seed oil, castor oil, sanddorn fruit oil, sand kernel oil, sesame oil, soybean oil, sunflower oil, grape seed oil, walnut oil, wild rose oil, wheat germ oil, and the liquid fractions of coconut oil and the like.

Other oils suitable for use in the powder additives contemplated herein include non-volatile silicone oils. Suitable non-volatile silicone oils include linear polyalkyl siloxanes, such as the polydimethylsiloxanes, and cetyldimethicones.

The powder additive comprises a non-volatile, saturated oil in an amount of about 0 wt. % to about 12 wt. % based on the total weight of the powder additive, according to an embodiment. In another embodiment, the powder additive contains a non-volatile, saturated oil in an amount of about 0.01 wt. % to about 5 wt. % based on the total weight of the powder additive.

As noted above, the powder additives contemplated herein are formulated to be added to coloring or bleaching agents, developers that typically include an oxidizing agent, such as, for example, hydrogen peroxide, or a combination of coloring or bleaching agents and developers before application to the hair. Accordingly, it is not necessary that the powder additives contain dye precursors, direct dyes, or oxidizing agents. In this regard, in an embodiment, should the powder additives contain dye precursors, direct dyes and/or oxidizing agents, they contain these ingredients in such amounts that the ingredients do not serve to contribute to the coloring or bleaching of the coloring or bleaching agents and/or developers to which the powder additives are added. In an embodiment, the powder additives contain no dye precursors, substantive dyes, or oxidizing agents.

As further noted above, the powder additives contemplated herein contain a maximum of about 10% by weight, preferably a maximum of about 6% by weight, of free water. In this regard, the powder additives are substantially non-aqueous. To this end, the powder additives do not require preservatives to maintain the quality of the powder additives and to extend shelf-life. In an embodiment, should the powder additives contain preservatives, they contain the preservatives in such amounts that a preservative effect is not achieved by the preservatives. In an embodiment, the powder additives contain no preservatives.

Methods for producing powder additives for bleaching and coloring agents also are provided herein. In accordance with an exemplary embodiment, the method includes passing each of the dry ingredients to be used in the powder additive, separately or together, through a milling machine, sieve, or mesh. The dry ingredients include any of the ingredients described above except the non-volatile, saturated oil. The milling machine, sieve, or mesh is configured to permit particles with an average particle size of less than 200 µm to pass therethrough. The particles can be separated using commonplace sieve or milling machines such as, for example, tumble, shaker or vibration sieves, hammer or ball mills, and the like. Commercial embodiments of suitable mills, sieves or meshes are available from, for example, Retsch GmbH of Germany.

The method continues, in accordance with an embodiment, by adding the dry ingredients of the powder additive in any desired sequence and mixing the ingredients during and/or after the adding until a homogeneous mixture is achieved. Mixing can continue as the ingredients are added or can be stopped before addition of an ingredient and restarted after the addition.

In an optional embodiment, during or after the mixing of the dry ingredients, the oil is sprayed on or otherwise applied to the dry ingredients. The oil, if solid at room temperature, first is heated to a liquid and then sprayed on or otherwise applied to the dry ingredients. The dry ingredients are stirred while the oil is applied thereto. Accordingly, the oil can be applied to the dry ingredients while the dry ingredients are being mixed together.

In another exemplary embodiment, after the ingredients have been combined, the mixture is passed through a milling machine, sieve, or mesh. The milling machine, sieve or mesh is configured to permit particles having an average particle size of less than 200 µm to pass therethrough. It will be appreciated that in accordance with another exemplary embodiment, the ingredients can be passed through a milling machine, sieve, or mesh both before and after mixing the ingredients, or once in accordance with yet another exemplary embodiment, either before mixing the ingredients or after mixing the ingredients.

The following is an exemplary embodiment of the powder additives contemplated herein, with each of the components set forth in weight percent of the total weight of the powder additive. The example is provided for illustration purposes only and is not meant to limit the various embodiments of the powder additives in any way. The powder additive of the below exemplary embodiment comprises particles of which at least 80% have an average particle size of less than 200 µm.

Example

| Ingredient | Wt. % |
|---|---|
| Sodium silicate $SiO_2$:$Na_2O$=2.0 | 29.0000 |
| Succinic acid | 60.0000 |
| Lysine HCl | 2.0000 |
| L-arginine | 2.0000 |
| Trimagnesium citrate | 3.0000 |
| Silicic acid pyrogen | 1.0000 |
| Glycine | 2.0000 |
| Keratin powder | 1.0000 |
| Total | 100% |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the subject matter in any way. Rather, the foregoing detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A powder additive for a keratin fiber coloring or bleaching agent or developer, the powder additive comprising:
   20 wt. % to about 80 wt. %, based on the total weight of the powder additive, of a dicarboxylic acid containing from about 2 to about 10 carbon atoms, selected from the group consisting of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof;
   an amino acid or a salt of an amino acid; and
   an alkalisilicate;
   wherein the powder additive has no greater than about 10% by weight water, based on the weight of the powder additive; and
   wherein the powder additive comprises particles and wherein at least about 80% of the particles have an average particle size of less than 200 µm.

2. The powder additive of claim 1, wherein the powder additive has no greater than about 6% by weight water, based on the weight of the powder additive.

3. The powder additive of claim 1, wherein the amino acid or the salt of an amino acid is selected from the group consisting of lysine and arginine.

4. The powder additive of claim 1, wherein the amino acid or the salt of an amino acid is present in an amount of about 0.01 wt. % to about 10 wt. %, based on the total weight of the powder additive.

5. The powder additive of claim 1, wherein the alkalisilicate is present in an amount of about 0.01 wt. % to about 60 wt. %, based on the total weight of the powder additive.

6. The powder additive of claim 1, further comprising silica, fumed silica, or both.

7. The powder additive of claim 6, wherein the silica, fumed silica or both are present in an amount of about 0.001 wt % to about 5 wt. %, based on the total weight of the powder additive.

8. The powder additive of claim 1, further comprising a protein hydrolysate.

9. The powder additive of claim 8, wherein the protein hydrolysate is present in an amount of about 0.2 wt % to about 2 wt %, based on the total weight of the powder additive.

10. The powder additive of claim 1, further comprising a polyvalent metal salt of an organic acid.

11. The powder additive of claim 1, further comprising a saturated, non-volatile oil.

12. The powder additive of claim 1, wherein the powder additive comprises 0 wt. % preservatives.

13. A powder additive for a keratin fiber coloring or bleaching agent or developer, the powder additive comprising:

20 wt. % to about 80 wt. %, based on the total weight of the powder additive, of a dicarboxylic acid containing from about 2 to about 10 carbon atoms, selected from the group consisting of malic acid, D-tartaric acid, L-tartaric acid, meso-tartaric acid, racemic acid, alpha-ketoglutaric acid, beta-ketoglutaric acid, oxaloacetic acid, maleic acid, fumaric acid, oxalic acid, malonic acid, succinic acid, glutaric acid, adipic acid, pimelic acid, azelaic acid, sorbic acid, a salt of these dicarboxylic acids, and mixtures thereof;

an amino acid or a salt of an amino acid;

an alkalisilicate;

a protein hydrolysate; and a polyvalent metal salt;

wherein the powder additive has no greater than about 10% by weight water, based on the weight of the powder additive; and wherein the powder additive comprises particles and wherein at least about 80% of the particles have an average particle size of less than 200 μm.

* * * * *